US006329541B1

(12) United States Patent
Jung et al.

(10) Patent No.: US 6,329,541 B1
(45) Date of Patent: Dec. 11, 2001

(54) ORGANO OMEGA-ALKENYL CYCLOPENTACARBYL SILANE-BRIDGED METALLOCENE COMPOUNDS

(75) Inventors: Michael Jung; Helmut G. Alt, both of Bayreuth (DE); M. Bruce Welch, Bartlesville, OK (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 08/969,876

(22) Filed: Nov. 14, 1997

Related U.S. Application Data

(63) Continuation of application No. 08/779,496, filed on Jan. 8, 1997, now abandoned.

(51) Int. Cl.[7] ....................................................... C07F 7/08
(52) U.S. Cl. ............................ 556/11; 556/465; 556/489; 524/15; 526/126; 526/127; 526/160; 526/470; 526/241; 526/351; 526/352; 526/348.4; 526/129; 534/15

(58) Field of Search .................................. 556/465, 489, 556/11; 534/15; 526/126, 127, 160, 170, 241, 351, 352, 348.4, 129

(56) References Cited

U.S. PATENT DOCUMENTS

| | | | |
|---|---|---|---|
| 5,169,818 | 12/1992 | Antberg et al. | 502/159 |
| 5,191,132 | 3/1993 | Patsidis et al. | 585/375 |
| 5,391,789 | 2/1995 | Rohrmann | 556/11 |
| 5,393,911 | 2/1995 | Patsidis et al. | 556/489 |
| 5,406,013 | 4/1995 | Patsidis et al. | 585/375 |
| 5,436,305 | 7/1995 | Alt et al. | 526/160 |
| 5,498,581 | 3/1996 | Welch et al. | 402/102 |
| 5,541,351 | 7/1996 | Patsidis et al. | 556/465 X |
| 5,565,592 | 10/1996 | Patsidis et al. | 556/11 |

FOREIGN PATENT DOCUMENTS

| | | |
|---|---|---|
| 0 604 908 A2 | 3/1994 | (EP) . |
| 0 586 167 A1 | 7/1994 | (EP) . |

*Primary Examiner*—Paul F. Shaver
(74) *Attorney, Agent, or Firm*—Edward L. Bowman

(57) ABSTRACT

An (organo) ((omega-alkenyl) cyclopentacarbyl) (silane-bridged) metallocene compound is provided. Polymerization processes therewith are also provided.

31 Claims, No Drawings

ORGANO OMEGA-ALKENYL CYCLOPENTACARBYL SILANE-BRIDGED METALLOCENE COMPOUNDS

This application is a File Wrapper Continuation of application Ser. No. 08/779,496, filed Jan. 8, 1997, now abandoned.

BACKGROUND OF THE INVENTION

In general, this invention is related to the fields of (organo) ((omega-alkenyl) cyclopentacarbyl) (silane bridged) metallocene compounds and processes that use (organo) ((omega-alkenyl) cyclopentacarbyl) (silane bridged) metallocene compounds.

The production of polymers that comprise ethylene is a multi-billion dollar enterprise. Many different catalysts can be used to polymerize ethylene. However, very few of these catalysts are of commercial importance. Currently, millions of dollars have been spent on research to make metallocene catalysts more commercially viable, and thus, more commercially important. This is because the polymers produced by such metallocene catalysts have properties that currently no other single polymer can reproduce. However, one of the technical problems associated with these metallocene catalysts is that they are homogenous with the polymerization medium. That is, they are soluble in the medium in which the polymerization is conducted. This is a drawback to the use of such metallocene catalysts because most commercially important polymerization processes use heterogenous catalysts. Therefore, in order to make metallocene catalysts more commercially important, heterogenous metallocene catalysts must be produced. Additionally, it is very important to have a metallocene catalyst that produces polymers that have a high molecular weight.

SUMMARY OF THE INVENTION

An object of this invention is to provide an (organo) ((omega-alkenyl) cyclopentacarbyl) (silane bridged) metallocene compound.

Another object of this invention is to provide a process to polymerize monomers, especially ethylene, with an (organo) ((omega-alkenyl) cyclopentacarbyl) (silane bridged) metallocene compound.

In accordance with one embodiment of this invention an (organo) ((omega-alkenyl) cyclopentacarbyl) (silane bridged) metallocene compound is provided.

In accordance with another embodiment of this invention a process to polymerize monomers, especially ethylene, with an (organo) ((omega-alkenyl) cyclopentacarbyl) (silane bridged) metallocene compound is provided. This process comprises (or optionally consists essentially of, or consists of): using an (organo) ((omega-alkenyl) cyclopentacarbyl) (silane bridged) metallocene compound to polymerize monomers into polymers.

The objects and advantages of this invention are further described and defined in the following description and claims. It should be noted that the invention described herein can be practiced without any components or steps not specifically detailed herein.

DETAILED DESCRIPTION OF THE INVENTION

In general, (organo) ((omega-alkenyl) cyclopentacarbyl) (silane bridged) metallocene compounds are those compounds having the general formula indicated in Box One.

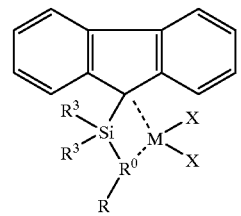

In this general formula, R is an $(R^1)_2C=C(R^1)-(C(R^1)_2)_n-C(R^1)_2-$group (where n is from 0 to about 20). In this group, each $R^1$ can be any substituent that does not substantially, and adversely, interfere with any of the processes disclosed herein. For example, each $R^1$ can be a hydrocarbyl having from 1 to about 20 carbon atoms. However, it is preferred that each $R^1$ have from 1 to 10 carbon atoms, and it is even more preferred that each $R^1$ have from 1 to 6 carbon atoms. Further examples of $R^1$ are hydrogen, alkyl, aryl, alkoxy, and aryloxy. Currently, it is most preferred if $R^1$ is hydrogen.

The R group is attached to a cyclopentacarbyl group ($R^0$) which can be either substituted or unsubstituted, and which can form a metallocene compound with a transition metal. The substituents of the cyclopentacarbyl group can be any substituent that does not substantially, and adversely, interfere with any of the processes disclosed herein. Examples of cyclopentacarbyl groups are substituted and unsubstituted cyclopentadiene groups and substituted and unsubstituted indenyl groups. Currently it is preferred if the cyclopentacarbyl group ($R^0$) is an indenyl.

The cyclopentacarbyl group is attached to a silane bridging group that can be substituted or unsubstituted. The substituents ($R^3$) of the silane bridging group can be any substituent that does not substantially, and adversely, interfere with any of the processes disclosed herein. Examples of such substituents are hydrogen, alkyl, aryl, alkoxy, and aryloxy. Currently, it is preferred if each $R^3$ is alkyl or aryl, however, it is most preferred if $R^3$ is aryl, such as, for example, phenyl.

The fluorenyl group in the general formula can be substituted or unsubstituted. The substituents of the fluorenyl group can be any substituent that does not substantially, and adversely, interfere with any of the processes disclosed herein. Examples of such substituents are hydrogen, alkyl, aryl, alkoxy, and aryloxy. Currently, it is preferred if the substituents are hydrogen.

In the general formula, M is a transition metal selected from the group consisting of titanium, zirconium, hafnium, vanadium, niobium, tantalum, chromium, molybdenum, tungsten, and the lanthanides. Currently, the preferred transition metals are zirconium and hafnium.

In the general formula, X is an alkyl, aryl, alkoxy, aryloxy, amides, hydride, or halogen. Currently, it is most preferred if X is a halogen. However, it is most preferred if X is chlorine.

This (organo) ((omega-alkenyl) cyclopentacarbyl) (silane bridged) metallocene compound can be produced by first taking a cyclopentacarbyl compound and reacting it with an organometal compound such as, for example, n-butyllithium, to form a cyclopentacarbyl metal compound. In general, the metal in the organometal compound is any Group I metal and the organo part of the compound is an alkyl. The cyclopentacarbyl compound is any compound that has at least five carbon atoms arranged in a cyclic structure. This cyclopentacarbyl compound can be either substituted or unsubstituted. Additionally, this cyclopentacarbyl compound can form a metallocene compound with a transition metal. The substituents of the cyclopentacarbyl compound can be any substituent that does not substantially, and adversely, interfere with any of the processes disclosed herein. Examples of cyclopentacarbyl compounds are substituted and unsubstituted cyclopentadiene groups and substituted and unsubstituted indenyl groups. In general, the reaction of the cyclopentacarbyl compound with an organometal compound to produce a cyclopentacarbyl metal is conducted at any suitable temperature and pressure. Currently, a temperature of about −80° C. to about 160° C. and a pressure of about 0 to about 100 atmospheres are preferred. However, a temperature of about −80° C. to about 60° C. and a pressure of about 1 atmosphere are more preferred. The molar ratio of cyclopentacarbyl compound to the organometal compound can be any suitable ratio. Currently, molar ratios of 1 to 1 are preferred.

This cyclopentacarbyl metal compound is then reacted with a haloalkene to produce an (omega-alkenyl) cyclopentacarbyl compound. In general, the reaction of the cyclopentacarbyl metal compound with a haloalkene to produce an (omega-alkenyl) cyclopentacarbyl compound is conducted at any suitable temperature and pressure. Currently, a temperature of about −80° C. to about 160° C. and a pressure of about 0 to about 100 atmospheres are preferred. However, a temperature of about −80° C. to about 60° C. and a pressure of about 1 atmosphere are more preferred. The molar ratio of cyclopentacarbyl metal compound to the haloalkene can be any suitable ratio. Currently, molar ratios of 1 to 1 are preferred.

Once the (omega-alkenyl) cyclopentacarbyl compound is produced it can be reacted with an organosilane to produce an (organo) ((omega-alkenyl) cyclopentacarbyl) (silane bridged) compound. In general, the reaction of the (omega-alkenyl) cyclopentacarbyl compound with an organosilane to produce an (organo) ((omega-alkenyl) cyclopentacarbyl) (silane bridged) compound is conducted at any suitable temperature and pressure. Currently, a temperature of about −80° C. to about 160° C. and a pressure of about 0 to about 100 atmospheres are preferred. However, a temperature of about −80° C. to about 60° C. and a pressure of about 1 atmosphere are more preferred. The molar ratio of cyclopentacarbyl metal compound to the haloalkene can be any suitable ratio. Currently, molar ratios of 1 to 1 are preferred.

Once the (organo) ((omega-alkenyl) cyclopentacarbyl) (silane bridged) compound is produced it can be used to produce metallocene compounds wherein the (omega-alkenyl) cyclopentacarbyl portion of the (organo) ((omega-alkenyl) cyclopentacarbyl) (silane bridged) compound is one of the ligands of the metallocene compound.

Various methods are known in the art to bind a ligand to a transition metal in order to produce a metallocene compound. For example, the following references can be consulted: U.S. Pat. Nos. 5,436,305; 5,498,581; 5,565,592; and European Application 524,624 (the entire disclosures of which are hereby incorporated by reference). In general, however, metallocene compounds that contain an (omega-alkenyl) (cyclopentacarbyl) can be prepared by reacting the (organo) ((omega-alkenyl) cyclopentacarbyl) (silane bridged) compound with an alkali metal alkyl compound to produce a ligand salt that is then reacted with a transition metal compound to yield a metallocene compound.

These metallocene compounds can be used to polymerize various olefins. The particular polymerization conditions employed using these compounds can vary depending upon the particular results desired. Usually these compounds are used with organoaluminoxane compounds, such as, for example, methylaluminoxane, to form better polymerization catalysts. The ratio of the transition metal to the organoaluminoxane composition can vary widely depending upon the particular composition selected and the results desired. Typically, the atomic ratio of aluminum in the organoaluminoxane composition to the transition metal is in the range of about 1/1 to about 20000/1, preferably about 15/1 to about 5000/1, and more preferably about 100/1 to about 1000/1.

Examples of some monomers for polymerization include ethylene and alpha-olefins having 3 to 20 carbon atoms, such as propylene, 1-butene, 3-methyl-1-butene, 3-methyl-1-pentene, 3-ethyl-1-hexene, 1-hexene, 4-methyl-1-pentene, 1-octene, 1-hexadecene, cyclopentene, norborene, styrene, 4-methyl styrene, vinyl cyclohexane, butadiene, and the like and mixtures thereof.

The present invention is particularly useful in slurry type polymerizations since it allows one to carry out such polymerizations more effectively than has heretofore been possible. A particularly preferred type of slurry polymerization involves the continuous loop reactor type polymerization wherein monomer, catalyst, and diluent, if employed, are continuously added to the reactor as needed and polymer product is continuously or at least periodically removed. Generally, in such processes, ethylene is polymerized in the presence of a suitable liquid diluent, a higher alpha-olefin comonomer, and optionally, hydrogen. The polymerization temperature can vary over the range which will allow for slurry polymerization. Often slurry polymerization will be conducted at a temperature in the range of about 50° C. to about 100° C., although higher and lower temperatures can be used.

One of the benefits of this invention is that during polymerization the metallocene compound is incorporated into the polymer chain thereby forming a heterogenous metallocene catalyst. As discussed above, this is a very important result because it increases the commercial importance of metallocene compounds. For example, a heterogenous metallocene catalyst can be formed by prepolymerizing these metallocene compounds with a monomer, such as, for example, ethylene, to form a prepolymer supported metallocene compound. Examples of such techniques are disclosed in U.S. Pat. No. 5,498,581, the entire disclosure of which is hereby incorporated by reference.

The following examples are provided to further illustrate this invention. However, the invention should not be construed to be limited to the particular embodiments in these examples.

EXAMPLES

All examples were carried out using standard Schlenk techniques with the exclusion of oxygen and air moisture under argon. The solvents were dried over either: (a) Na/K alloy for ether, hexane, pentane, tetrahydrofuran, and toluene; (b) $P_4O_{10}$ for methylene chloride; or (c) magnesium for methanol; and then distilled under argon.

Example One

PREPARATION OF AN ((OMEGA-ALKENYL) CYCLOPENTACARBYL) COMPOUND

Example 1-1

Ten mL (85.7 mmol) of indene, which is a cyclopentacarbyl compound, was added to a container that contained 150 mL of diethyl ether and 15 mL of tetrahydrofuran to form a first mixture. This first mixture was then reacted with 53.6 mL (85.7 mmol) of n-butyllithium (1.6 M in hexane) to form indenyllithium, which is a cyclopentacarbyl metal compound. This reaction took place at −78° C. A yellow solution was formed. This yellow solution was then stirred at room temperature (about 25° C.) for four hours and then cooled again to −78° C. An equivalent quantity of 1-bromopropene, a haloalkene compound, was added dropwise to the yellow solution to form a second mixture. This second mixture was then stirred overnight at room temperature (about 25° C.). Thereafter, this second mixture was then hydrolyzed with 50 mL of water to form an organic phase and a water phase. The organic phase was dried over sodium sulfate and then the solvent was evaporated under a vacuum to produce a third mixture. This third mixture was then distilled using a high vacuum ($10^{-2}$ torr) to obtain a product. The product obtained was allyl-1-indene, which is an ((omega-alkenyl) cyclopentacarbyl) compound.

Example 1-2

Ten mL (85.7 mmol) of indene, which is a cyclopentacarbyl compound, was added to a container that contained 150 mL of diethyl ether and 15 mL of tetrahydrofuran to form a first mixture. This first mixture was then reacted with 53.6 mL (85.7 mmol) of n-butyllithium (1.6 M in hexane) to form indenyllithium, which is a cyclopentacarbyl metal compound. This reaction took place at −78° C. A yellow solution was formed. This yellow solution was then stirred at room temperature (about 25° C.) for four hours and then cooled again to −78° C. An equivalent quantity of 1-bromohexene, a haloalkene compound, was added dropwise to the yellow solution to form a second mixture. This second mixture was then stirred overnight at room temperature (about 25° C.). Thereafter, this second mixture was then hydrolyzed with 50 mL of water to form an organic phase and a water phase. The organic phase was dried over sodium sulfate and then the solvent was evaporated under a vacuum to produce a third mixture. This third mixture was then distilled using a high vacuum ($10^{-2}$ torr) to obtain a product. The product obtained was 5-hexenyl-1-indene, which is an ((omega-alkenyl) cyclopentacarbyl) compound.

Example Two

PREPARATION OF AN (ORGANO) ((OMEGA-ALKENYL) CYCLOPENTACARBYL) SILANE COMPOUND

Example 2-1

Ten mmol of allyl-1-indene (in 60 mL of diethyl ether) was reacted with 6.25 mL of butyllithium (1.6 M solution in hexane) to form a first mixture. This first mixture was then stirred for four hours. After stirring, 2.58 grams (10 mmol) of (9-fluorenyl) (dimethyl) (chloro) silane, which is an organosilane, was added to the first mixture to form a second mixture. This second mixture was then stirred overnight. The second mixture was then hydrolyzed with 50 mL of water to form a water phase and an organic phase. The organic phase was then dried over sodium sulfate followed by evaporation of the organic phase to leave the product, which was a yellow oil. This product was ((3-allyl) indenyl) (dimethyl) (9-fluorenyl) silane, which is an (organo) ((omega-alkenyl) cyclopentacarbyl) silane compound.

Example 2-2

Ten mmol of 5-hexenyl-1-indene (in 60 mL of diethyl ether) was reacted with 6.25 mL of butyllithium (1.6 M solution in hexane) to form a first mixture. This first mixture was then stirred for four hours. After stirring, 2.58 grams (10 mmol) of (9-fluorenyl) (dimethyl) (chloro) silane, which is an organosilane, was added to the first mixture to form a second mixture. This second mixture was then stirred overnight. The second mixture was then hydrolyzed with 50 mL of water to form a water phase and an organic phase. The organic phase was then dried over sodium sulfate followed by evaporation of the organic phase to leave the product, which was a yellow oil. This product was ((3-hex-5-enyl) indenyl) (dimethyl) (9-fluorenyl) silane, which is an (organo) ((omega-alkenyl) cyclopentacarbyl) silane compound.

Example 2-3

Ten mmol of allyl-1-indene (in 60 mL of diethyl ether) was reacted with 6.25 mL of butyllithium (1.6 M solution in hexane) to form a first mixture. This first mixture was then stirred for four hours. After stirring, 3.83 grams (10 mmol) of (9-fluorenyl) (diphenyl) (chloro) silane, which is an organosilane, was added to the first mixture to form a second mixture. This second mixture was then stirred overnight. The second mixture was then hydrolyzed with 50 mL of water to form a water phase and an organic phase. The organic phase was then dried over sodium sulfate followed by concentration of the organic phase. The product was precipitated as a white powder. This product was ((3-allyl) indenyl) (diphenyl) (9-fluorenyl) silane, which is an (organo) ((omega-alkenyl) cyclopentacarbyl) silane compound.

Example 2-4

Ten mmol of 5-hexenyl-1-indene (in 60 mL of diethyl ether) was reacted with 6.25 mL of butyllithium (1.6 M solution in hexane) to form a first mixture. This first mixture was then stirred for four hours. After stirring, 3.83 grams (10 mmol) of (9-fluorenyl) (diphenyl) (chloro) silane, which is an organosilane, was added to the first mixture to form a second mixture. This second mixture was then stirred overnight. The second mixture was then hydrolyzed with 50 mL of water to form a water phase and an organic phase. The organic phase was then dried over sodium sulfate followed by concentration of the organic phase. The product was precipitated as a white powder. This product was ((3-hex-5-enyl) indenyl) (diphenyl) (9-fluorenyl) silane, which is an (organo) ((omega-alkenyl) cyclopentacarbyl) silane compound.

Example Three

PREPARATION OF A METALLOCENE COMPOUND THAT CONTAINS AN (ORGANO) ((OMEGA-ALKENYL) CYCLOPENTACARBYL) SILANE COMPOUND

Example 3-1

One gram of ((3-allyl) indenyl) (dimethyl) (9-fluorenyl) silane was mixed with 40 mL of diethyl ether to form a first mixture. This first mixture was stirred with 2 equivalents of n-butyllithium (1.6M in hexane) for about eight hours at room temperature (about 25° C.) to form a second mixture. Thereafter, an equivalent of zirconium tetrachloride was added to the second mixture and stirred overnight to form a first product. This second product was (1-(3-allyl) indenyl) (dimethyl) (9-fluorenyl) silane zirconium dichloride, a metallocene compound.

Example 3-2

One gram of ((3-hex-5-enyl) indenyl) (dimethyl) (9-fluorenyl) silane was mixed with 40 mL of diethyl ether to form a first mixture. This first mixture was stirred with 2 equivalents of n-butyllithium (1.6M in hexane) for about eight hours at room temperature (about 25° C.) to form a second mixture. Thereafter, an equivalent of zirconium tetrachloride was added to the second mixture and stirred overnight to form a first product. This second product was (1-(3-hex-5-enyl) indenyl) (dimethyl) (9-fluorenyl) silane zirconium dichloride, a metallocene compound.

Example 3-3

One gram of ((3-allyl) indenyl) (diphenyl) (9-fluorenyl) silane was mixed with 40 mL of diethyl ether to form a first mixture. This first mixture was stirred with 2 equivalents of n-butyllithium (1.6M in hexane) for about eight hours at room temperature (about 25° C.) to form a second mixture. Thereafter, an equivalent of zirconium tetrachloride was added to the second mixture and stirred overnight to form a first product. This second product was (1-(3-allyl) indenyl) (diphenyl) (9-fluorenyl) silane zirconium dichloride, a metallocene compound.

Example 3-4

One gram of ((3-hex-5-enyl) indenyl) (diphenyl) (9-fluorenyl) silane was mixed with 40 mL of diethyl ether to form a first mixture. This first mixture was stirred with 2 equivalents of n-butyllithium (1.6M in hexane) for about eight hours at room temperature (about 25° C.) to form a second mixture. Thereafter, an equivalent of zirconium tetrachloride was added to the second mixture and stirred overnight to form a first product. This second product was (1-(3-hex-5-enyl) indenyl) (diphenyl) (9-fluorenyl) silane zirconium dichloride, a metallocene compound.

Example Four

POLYMERIZATION OF ETHYLENE WITH A METALLOCENE COMPOUND THAT CONTAINS AN (ORGANO) ((OMEGA-ALKENYL) CYCLOPENTACARBYL) SILANE COMPOUND

Example 4-1

About 10 mg of (1-(3-allyl) indenyl) (dimethyl) (9-fluorenyl) silane zirconium dichloride was mixed with 10 mL of methylaluminoxane (30 weight percent in toluene) to form a catalyst complex and then diluted with 10 mL of toluene. The polymerization of ethylene was carried out in a 1 L Buechi laboratory autoclave. The autoclave was filled with 500 mL of pentane and 7 mL of methylaluminoxane. An amount (about $1.8 \times 10^{-6}$ mol) of catalyst complex was then added to the autoclave. The autoclave thermostat was then set to 60° C. and a constant ethylene pressure of 10 bar was applied. The reactor was stirred at 800 rpm. The polymerization was stopped after one hour. About 71 grams of polyethylene was recovered. The molecular weight of the polymer was 350,000. This visometric mean molecular weight was determined with a precision capillary viscometer in Decalin at 135° C. Calibration curves were available for determination of the molecular weight. However, the insoluble components were separated before the measurement of the molecular weight therefore the value determined is not an absolute value, but does give an indication of the trend of the molecular weight. All of the following molecular weights were determined using this technique.

Example 4-2

About 10 mg of (1-(3-hex-5-enyl) indenyl) (dimethyl) (9-fluorenyl) silane zirconium dichloride was mixed with 10 mL of methylaluminoxane (30 weight percent in toluene) to form a catalyst complex and then diluted with 10 mL of toluene. The polymerization of ethylene was carried out in a 1 L Buechi laboratory autoclave. The autoclave was filled with 500 mL of pentane and 7 mL of methylaluminoxane. An amount (about $1.7 \times 10^{-6}$ mol) of catalyst complex was then added to the autoclave. The autoclave thermostat was then set to 60° C. and a constant ethylene pressure of 10 bar was applied. The reactor was stirred at 800 rpm. The polymerization was stopped after one hour. About 45 grams of polyethylene was recovered. The molecular weight of the polymer was 385,000.

Example 4-3

About 10 mg of (1-(3-allyl) indenyl) (diphenyl) (9-fluorenyl) silane zirconium dichloride was mixed with 10 mL of methylaluminoxane (30 weight percent in toluene) to form a catalyst complex and then diluted with 10 mL of toluene. The polymerization of ethylene was carried out in a 1 L Buechi laboratory autoclave. The autoclave was filled with 500 mL of pentane and 7 mL of methylaluminoxane. An amount (about $1.5 \times 10^{-6}$ mol) of catalyst complex was then added to the autoclave. The autoclave thermostat was then set to 60° C. and a constant ethylene pressure of 10 bar was applied. The reactor was stirred at 800 rpm. The polymerization was stopped after one hour. About 40 grams of polyethylene was recovered. The molecular weight of the polymer was 580,000.

Example 4-4

About 10 mg of (1-(3-hex-5-enyl) indenyl) (diphenyl) (9-fluorenyl) silane zirconium dichloride was mixed with 10 mL of methylaluminoxane (30 weight percent in toluene) to form a catalyst complex and then diluted with 10 mL of toluene. The polymerization of ethylene was carried out in a 1 L Buechi laboratory autoclave. The autoclave was filled with 500 mL of pentane and 7 mL of methylaluminoxane. An amount (about $1.5 \times 10^{-6}$ mol) of catalyst complex was then added to the autoclave. The autoclave thermostat was then set to 60° C. and a constant ethylene pressure of 10 bar was applied. The reactor was stirred at 800 rpm. The polymerization was stopped after one hour. About 76 grams of polyethylene was recovered. The molecular weight of the polymer was 480,000.

Example Five

POLYMERIZATION OF ETHYLENE WITH A METALLOCENE COMPOUND THAT CONTAINS AN (ORGANO) ((OMEGA-ALKENYL) CYCLOPENTACARBYL) SILANE COMPOUND TO FORM A HETEROGENOUS CATALYST COMPLEX

Example 5-1

In a Schlenk tube (1-(3-allyl) indenyl) (dimethyl) (9-fluorenyl) silane zirconium dichloride was mixed with methylaluminoxane and toluene to form a catalyst complex. This catalyst complex was then exposed to an ethylene pressure of 0.4 to 0.6 bar to incorporate the catalyst complex into an ethylene polymer chain thereby forming a heterogenous metallocene catalyst.

Example 5-2

In a Schlenk tube (1-(3-hex-5-enyl) indenyl) (dimethyl) (9-fluorenyl) silane zirconium dichloride was mixed with methylaluminoxane and toluene to form a catalyst complex.

This catalyst complex was then exposed to an ethylene pressure of 0.4 to 0.6 bar to incorporate the catalyst complex into an ethylene polymer chain thereby forming a heterogenous metallocene catalyst.

Example 5-3

In a Schlenk tube (1-(3-allyl) indenyl) (diphenyl) (9-fluorenyl) silane zirconium dichloride was mixed with methylaluminoxane and toluene to form a catalyst complex. This catalyst complex was then exposed to an ethylene pressure of 0.4 to 0.6 bar to incorporate the catalyst complex into an ethylene polymer chain thereby forming a heterogenous metallocene catalyst.

Example 5-4

In a Schlenk tube (1-(3-hex-5-enyl) indenyl) (diphenyl) (9-fluorenyl) silane zirconium dichloride was mixed with methylaluminoxane and toluene to form a catalyst complex. This catalyst complex was then exposed to an ethylene pressure of 0.4 to 0.6 bar to incorporate the catalyst complex into an ethylene polymer chain thereby forming a heterogenous metallocene catalyst.

Comparative Example

In a Schlenk tube (9-fluorenyl) (5-hexenyl) (1-indenyl) (methyl) silane zirconium dichloride was mixed with methylaluminoxane and toluene to form a catalyst complex. This catalyst complex was then exposed to an ethylene pressure of 0.4 to 0.6 bar to incorporate the catalyst complex into an ethylene polymer chain thereby forming a heterogenous metallocene catalyst.

The polymerization of ethylene was carried out in a 1 L Buechi laboratory autoclave. The autoclave was filled with 500 mL of pentane and 7 mL of methylaluminoxane. An amount (about $1.8 \times 10^{-6}$ mol) of catalyst complex was then added to the autoclave. The autoclave thermostat was then set to 60° C. and a constant ethylene pressure of 10 bar was applied. The reactor was stirred at 800 rpm. The polymerization was stopped after one hour. About 52 grams of polyethylene was recovered. The molecular weight of the polymer was 270,000.

Discussion of the Examples

In Example 4-2, (1-(3-hex-5-enyl) indenyl) (dimethyl) (9-fluorenyl) silane zirconium dichloride was used to polymerize ethylene. In the comparative example (9-fluorenyl) (5-hexenyl) (1-indenyl) (methyl) silane zirconium dichloride was used to polymerize ethylene. The main difference between these two compounds is that the former has an omega-hexene group on the indenyl, whereas, the latter has an omega-hexene group on the bridging silane group. While this difference might seem minor to those unskilled in the art, the difference in the molecular weight of the polymers produced by each catalyst is unexpected and unobvious. That is, the former compound polymerizes ethylene to form a polymer having a molecular weight 43 percent greater than the latter.

In Example 4-4, (1-(3-hex-5-enyl) indenyl) (diphenyl) (9-fluorenyl) silane zirconium dichloride was used to polymerize ethylene. In Example 4-2, (1-(3-hex-5-enyl) indenyl) (dimethyl) (9-fluorenyl) silane zirconium dichloride was used to polymerize ethylene. The main difference between these two compounds is that the former has phenyl groups on the bridging silane group, whereas, the latter has methyl groups on the bridging silane group. While this difference might seem minor to those unskilled in the art, the difference in the molecular weight of the polymers produced by each catalyst is unexpected and unobvious. That is, the former compound polymerizes ethylene to form a polymer having a molecular weight 25 percent greater than the latter.

That which is claimed:

1. A composition of matter being a metallocene having the following formula:

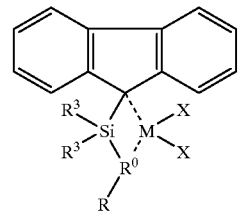

wherein M is a transition metal selected from group consisting of titanium, zirconium, hafnium, vanadium, niobium, tantalum, chromium, molybdenum, tungsten, and the lanthanides; and wherein each X is a halide wherein R is an $(R^1)_2C=C(R^1)-(C(R^1)_2)_n-C(R^1)_2$-group, and wherein n is from 0 to about 20, and wherein each $R^1$ is selected from hydrogen or hydrocarbyl groups having from 1 to about 20 carbon atoms; and wherein each $R^3$ is the same or different and is selected from methyl and phenyl; and wherein $R^0$ is an indenyl group.

2. A composition according to claim 1 wherein M is selected from the group consisting of zirconium and hafnium.

3. A composition according to claim 1 wherein M is zircomum.

4. A composition according to claim 3 wherein X is chlorine.

5. A composition according to claim 4 having the name (1-(3-allyl) indenyl) (dimethyl) (9-fluorenyl) silane zirconium dichloride.

6. A composition according to claim 4 having the name (1(3-allyl) indenyl) (diphenyl) (9-fluorenyl) silane zirconium dichloride.

7. A composition according to claim 4 having the name (1-(3-hex-5-enyl) indenyl) diphenyl) (9-fluorenyl) silane zirconium dichloride.

8. A composition according to claim 4 having the name (10(3-hex-5-enyl) indenyl) (dimethyl) (9-fluorenyl) silane zirconium dichloride.

9. A catalyst composition resulting from the combination of a metallocene of claim 1 and an organoaluminoxane.

10. A catalyst composition according to claim 9 wherein m is zirconium and X is chlorine.

11. A catalyst composition according to claim 10 wherein said organoaluminoxane is methylaluminoxane.

12. A catalyst according to claim 11 wherein the metallocene is (1-(3-allyl) indenyl) (dimethyl) (9-fluorenyl) silane zirconium dichloride.

13. A catalyst according to claim 11 wherein the metallocene is (1-(3-allyl) indenyl) (diphenyl) (9-fluorenyl) silane zirconium dichloride.

14. A catalyst according to claim 11 wherein the metallocene is (1-(3-hex-5-enyl) indenyl) diphenyl) (9-fluorenyl) silane zirconium dichloride.

15. A catalyst according to claim 11 wherein the metallocene is (1-(3-hex-5-enyl) indenyl) (dimethyl) (9-fluorenyl) silane zirconium dichloride.

16. A catalyst composition according to claim 9 comprising a solid prepared by contacting a metallocene of claim 1, an organoaluminoxane, and ethylene under suitable polymerization conditions.

17. A catalyst composition according to claim 16 wherein said organoaluminoxane is methylaluminoxane.

18. A catalyst according to claim 17 wherein the metallocene is (1-(3-allyl) indenyl) (dimethyl) (9-fluorenyl) silane zirconium dichloride.

19. A catalyst according to claim 17 wherein the metallocene is (1-(3-allyl) indenyl) (diphenyl) (9-fluorenyl) silane zirconium dichloride.

20. A catalyst according to claim 17 wherein the metallocene is (1-(3-hex-5-enyl) indenyl) diphenyl) (9-fluorenyl) silane zirconium dichloride.

21. A catalyst according to claim 17 wherein the metallocene is (1-(3-hex-5-enyl) indenyl) (dimethyl) (9-fluorenyl) silane zirconium dichloride.

22. A process for forming a polymer comprising contacting ethylenes and optionally one or more alpha-olefins 3 to 20 carbon atoms with a catalyst composition of claim 9 under suitable polymerization conditions.

23. A process according to claim 22 wherein the metallocene of the catalyst system is (1-(3-allyl) indenyl) (dimethyl) (9-fluorenyl) silane zirconium dichloride.

24. A process according to claim 22 wherein the metallocene of the catalyst system is (1-(3-allyl) indenyl) (diphenyl) (9-fluorenyl) silane zirconium dichloride.

25. A process according to claim 22 wherein the metallocene of the catalyst system is (1-(3-hex-5-enyl) indenyl) diphenyl) (9-fluorenyl) silane zirconium dichloride.

26. A process according to claim 22 wherein the metallocene of the catalyst system is (1-(3-hex-5-enyl) indenyl) (dimethyl) (9-fluorenyl) silane zirconium dichloride.

27. A process for forming a polymer comprising contacting ethylenes and optionally one or more alpha-olefins 3 to 20 carbon atoms with a catalyst composition of claim 16 under suitable polymerization conditions.

28. A process according to claim 27 wherein the metallocene of the catalyst system is (1-(3-allyl) indenyl) (diphenyl) (9-fluorenyl) silane zirconium dichloride.

29. A process according to claim 27 wherein the metallocene of the catalyst system is (1-(3-hex-5-enyl) indenyl) diphenyl) (9-fluorenyl) silane zirconium dichloride.

30. A process according to claim 27 wherein the metallocene of the catalyst system is (1-(3-hex-5-enyl) indenyl) (dimethyl) (9- fluorenyl) silane zirconium dichloride.

31. A process according to claim 22 wherein the metallocene of the catalyst system is (1-(3-allyl) indenyl) (dimethyl) (9-fluorenyl) silane zirconium dichloride.

\* \* \* \* \*